United States Patent
Lin et al.

(10) Patent No.: US 11,253,541 B2
(45) Date of Patent: Feb. 22, 2022

(54) **METHOD OF INHIBITING INFLAMMATORY RESPONSE USING LIPOPOLYSACCHARIDE OF *PARABACTEROIDES GOLDSTEINII***

(71) Applicant: Multistars Biotechnology Company Limited, Taoyuan (TW)

(72) Inventors: Tzu-Lung Lin, Taoyuan (TW); Po-I Wu, Taoyuan (TW)

(73) Assignee: MULTISTARS BIOTECHNOLOGY COMPANY LIMITED, Taoyuan (TW)

( * ) Notice: Subject to any disclaimer, the term of this patent is extended or adjusted under 35 U.S.C. 154(b) by 0 days.

(21) Appl. No.: 16/747,904

(22) Filed: Jan. 21, 2020

(65) Prior Publication Data

US 2020/0237806 A1 Jul. 30, 2020

Related U.S. Application Data

(60) Provisional application No. 62/796,599, filed on Jan. 25, 2019.

(30) Foreign Application Priority Data

Dec. 31, 2019 (TW) ................................. 108148713

(51) Int. Cl.
*A61K 31/739* (2006.01)
*A61P 37/02* (2006.01)
*A61K 35/74* (2015.01)

(52) U.S. Cl.
CPC ............ *A61K 31/739* (2013.01); *A61K 35/74* (2013.01); *A61P 37/02* (2018.01)

(58) Field of Classification Search
CPC .. A61K 31/739; A61K 35/74; A61P 37/00–08
See application file for complete search history.

(56) References Cited

PUBLICATIONS

Wu, T. et al "Gut commensal Parabacteroides goldsteinii plays a predominant role . . . " Gut, vol. 68, pp. 248-262. (Year: 2019).*
Neyrinck, A. et al "Rhubarb extract prevents hepatic inflammation . . . " Mol. Nutr. Food Res., vol. 61, No. 1, pp. 1-12. (Year: 2017).*

\* cited by examiner

*Primary Examiner* — Leigh C Maier
(74) *Attorney, Agent, or Firm* — WPAT, PC

(57) ABSTRACT

The present invention describes a method of inhibiting inflammatory response by using a lipopolysaccharide of *Parabacteroides goldsteinii*. The lipopolysaccharide of *Parabacteroides goldsteinii* can effectively inhibit the immune responses caused by pathogenic lipopolysaccharides in peripheral blood mononuclear cells, macrophages, and/or B cells, and then can be effectively used to inhibit the inflammatory responses and the preparation of the related compositions.

9 Claims, 7 Drawing Sheets

| gene | P. goldsteinii MTS01 | E. coli MG1655 | identity | E value | B. dorei DSM17855 | identity | E value |
|---|---|---|---|---|---|---|---|
| lpxA | gene_109 \| - \|129555\|130340 | b0180 | 41% | 4e-58 | BACDOR_00466 | 59% | 5e-108 |
| lpxC | gene_110 \| - \|130359\|131744 | b0096 | 37% | 1e-49 | BACDOR_00467 | 74% | 0 |
| lpxD | gene_111 \| - \|131756\|132796 | b0179 | 36% | 2e-66 | BACDOR_00468 | 59% | 6e-160 |
| lpxH | gene_4908 \| - \|6158554\|6159327 | b0524 | 22% | 6e-08 | BACDOR_01244 | 56% | 8e-100 |
| lpxB | gene_5050 \| - \|6316231\|6317364 | b0182 | 31% | 3e-46 | BACDOR_03148 | 63% | 4e-172 |
| lpxK | gene_160 \| - \|179657\|180601 | b0915 | 27% | 6e-23 | BACDOR_02449 | 46% | 2e-94 |
| lpxA | gene_5441 \| - \|6810828\|6812066 | b3633 | 26% | 3e-35 | BACDOR_02423 | 57% | 1e-169 |
| lpxL | gene_11 \| - \|13421\|14302 | b1054 | 23% | 2e-11 | BACDOR_01792 | 39% | 2e-71 |
| lpxM | - | b1855 | - | - | - | - | - |

FIG. 1B

METHOD OF INHIBITING INFLAMMATORY RESPONSE USING LIPOPOLYSACCHARIDE OF *PARABACTEROIDES GOLDSTEINII*

CROSS-REFERENCE TO RELATED APPLICATION

This application claims priority of U.S. provisional application No. 62/796,599, filed on Jan. 25, 2019, and priority of Taiwan patent application No. 108148713, filed on Dec. 31, 2019 the content of which are incorporated herein in its entirety by reference.

BACKGROUND OF THE INVENTION

1. Field of the Invention

The present invention relates to a method of using a lipopolysaccharide of *Parabacteroides goldsteinii*, in particular to the use of the lipopolysaccharide of *Parabacteroides goldsteinii* to inhibit inflammatory response; wherein, the lipopolysaccharide of *Parabacteroides goldsteinii* can effectively inhibit the immune response of peripheral blood mononuclear cells, macrophages and/or B cells to effectively inhibit the occurrence of inflammatory response.

2. The Prior Art

Inflammatory response is a defensive response of vascular system tissues to inflammatory factors and local damage. It is mainly a physiological response triggered by stimuli such as trauma, bleeding or pathogen infection, including symptoms of redness, swelling, fever, pain, etc. Inflammatory response is a protective measure of the innate immune system to remove harmful stimuli or pathogens and promote tissue repair. Usually, the inflammatory response is beneficial.

Lipopolysaccharide (LPS) is one of the main components on the cell membrane of Gram-negative bacteria, and it is also a marker of bacterial invasion, and it is an endotoxin. LPS mainly provides and maintains the structural integrity of bacteria, and protects the cell membrane of bacteria from attack by certain chemicals, such as the immune response from the host. When a microorganism invades an individual and releases a large amount of lipopolysaccharide, it stimulates immune cells to secrete a large number of cytokine that promote inflammatory response, such as tumor necrosis factor-α (TNF-α), interleukin-1 (Interleukin-1, IL-1), etc., and cause individuals to produce excessive inflammatory response, and even lead to the occurrence of sepsis, the most serious may be fatal, and the biological response induced by lipopolysaccharide is considered to be the main cause of sepsis.

However, about 110,000 people still suffer from sepsis every year in Taiwan, with an average of 300 new cases every day. As the elderly population grows, the number of immunosuppressed patients increases, the number of invasive treatment tests increases, and microbial resistance increases, the number of cases of sepsis is currently on the rise, and despite the development of medicine so far, the mortality rate of severe sepsis is still as high as 30 to 40 percent.

Therefore, to sum up, in response to the high incidence and mortality of sepsis and based on the improvement of modern living standards and the improvement of the concept of health care, it is really necessary to develop a composition that is convenient and effective in the front-end to slow down the immune response or to suppress the inflammatory response caused by pathogens.

SUMMARY OF THE INVENTION

One objective of the present invention is to provide a method of inhibiting an inflammatory response, comprising administering to a subject in need thereof a composition comprising an effective amount of a lipopolysaccharide of a *Parabacteroides goldsteinii*.

In one embodiment of the present invention, the lipopolysaccharide of the *Parabacteroides goldsteinii* inhibits an immune response of a peripheral blood mononuclear cell and inhibits the peripheral blood mononuclear cell secretes a cytokine.

In one embodiment of the present invention, the lipopolysaccharide of the *Parabacteroides goldsteinii* inhibits an immune response of a macrophage and inhibits the macrophage secretes a cytokine.

In one embodiment of the present invention, the lipopolysaccharide of the *Parabacteroides goldsteinii* inhibits an immune response of a B cell and inhibits the B cell differentiates or secretes a cytokine.

In one embodiment of the present invention, the inflammatory response is induced by a pathogenic lipopolysaccharide, and the pathogenic lipopolysaccharide is from an *Escherichia coli*.

In one embodiment of the present invention, the *Parabacteroides goldsteinii* is *Parabacteroides goldsteinii* DSM32939.

The use of the lipopolysaccharide of the *Parabacteroides goldsteinii* of the present invention in the inhibition of inflammatory response can be, but is not limited to, oral administration to the subject in need thereof. The composition can be orally administered along with food; therefore, the preparation of the composition comprising the *Parabacteroides goldsteinii* of the present invention can further include a protein, a monosaccharide, a disaccharide, an oligosaccharide, an oligosaccharide, a polysaccharide, a carbohydrate, an amino acid, a lipid, a vitamin, or any combination thereof, and the composition further comprises a pharmaceutically acceptable excipient, carrier, adjuvant, and/or food additive.

Otherwise, the preparation of the composition comprising the lipopolysaccharide of the *Parabacteroides goldsteinii* of the present invention can further comprise a pharmaceutically acceptable carrier or another adjuvant well-known in the art. The composition is in the form of, but is not limited to, a spray gas, a solution, a semi-solid, a solid, a gelatin capsule, a soft capsule, a tablet, an oral strip, a chewing gum, and/or a freeze-dried powder in order to deliver the lipopolysaccharide of the *Parabacteroides goldsteinii* of the present invention to the intestinal tract or to partially or fully colonize to the intestinal tract of subjects. Simultaneously, the lipopolysaccharide of the *Parabacteroides goldsteinii* of the present invention can further use in the preparation of a food, a health food, or a dietary supplement.

The invention provides a method of inhibiting an inflammatory response, comprising administering to a subject in need thereof a composition comprising an effective amount of a lipopolysaccharide of a *Parabacteroides goldsteinii*. In the *Parabacteroides goldsteinii* of the present invention, the sequence position of orthologous gens corresponding to the gene of LpxA, LpxC, LpxD, LpxH, LpxB, LpxK, KdtA, and LpxL to the lipid A known in *E. coli* could be found, except LpxM. However, these genes have low identity with *E. coli* MG1655 strain and *Bacteroides* dorei DSM17855 strain.

The lipopolysaccharide of *Parabacteroides goldsteinii* of the present invention would not stimulate the secretion of interleukin-1β by peripheral blood mononuclear cells, the secretion of TNF-α by macrophages, and would not induce the Naïve B to express surfaces antigen CD86 and to proliferate, which represent the Naïve B cells are induced to differentiate, indicating that the lipopolysaccharide of *Parabacteroides goldsteinii* DSM32939 of the present invention would not cause an immune response in peripheral blood mononuclear cells, macrophages, or B cells, that is, it has low endo-toxicity to individuals. Furthermore, the lipopolysaccharide of *Parabacteroides goldsteinii* of the present invention can inhibit the immune response induced by the lipopolysaccharide of *E. coli* in human peripheral blood mononuclear cells, macrophages, or B cells, and has anti-inflammatory activity in peripheral blood mononuclear cells, macrophages, or B cells, and has immunosuppressive ability. Therefore, the lipopolysaccharide of *Parabacteroides goldsteinii* of the present invention can be used for inhibiting the immune response and the preparation of the compositions thereof, and in particular, it can inhibit the inflammatory response caused by pathogenic lipopolysaccharide.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

BRIEF DESCRIPTION OF THE DRAWINGS

FIG. 1B shows the BLAST analysis results of the *Parabacteroides goldsteinii* of one embodiment of the present invention.

DETAILED DESCRIPTION OF THE PREFERRED EMBODIMENT

Figure 1A:
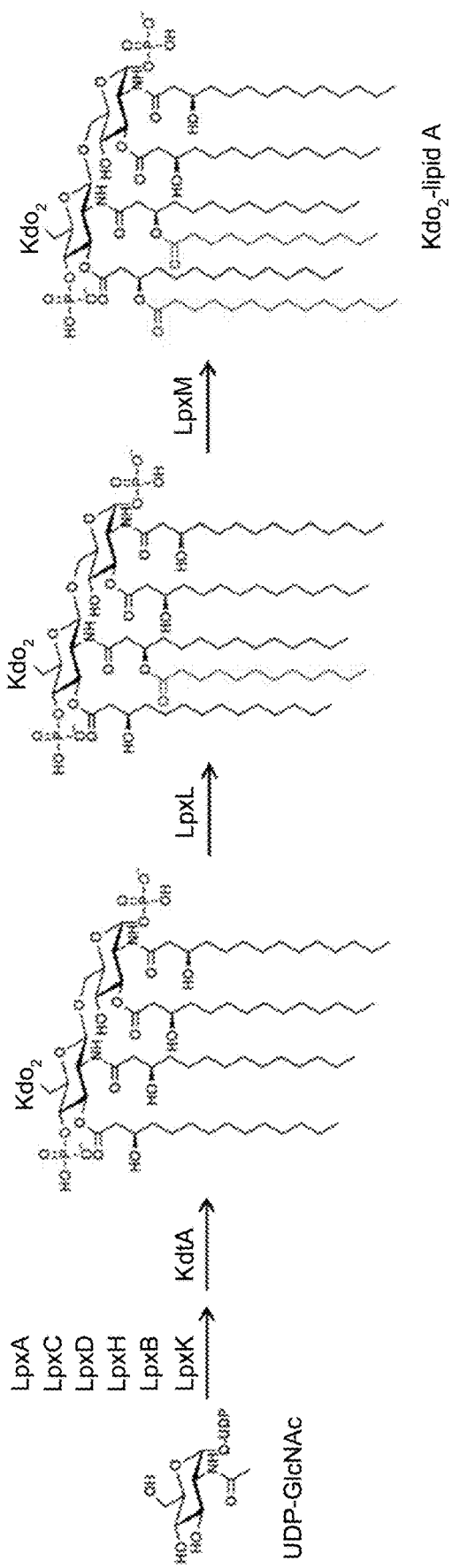
FIG. 1A shows the reaction formula of the biochemical synthesis pathway of $Kdo_2$-lipid in *E. coli*.

Statistical analysis is performed by Excel software. Data are expressed as mean±standard deviation (SD), and differences between groups are statistically analyzed by one-way ANOVA.

The data provides in the present invention represent approximated, experimental values that vary within a range of ±20%, preferably ±10%, and most preferably ±5%.

According to the present invention, the pharmaceutical composition can be manufactured into a dosage form suitable for parenterally or orally administration using techniques well known to those having skill in the art, including, but not limited to, an injection, for example, sterile aqueous solutions or dispersions, a sterile powder, an external preparation and the like.

According to the present invention, the pharmaceutical composition could further comprise a pharmaceutically acceptable carrier that is widely used in pharmaceutical manufacturing techniques. For example, the pharmaceutically acceptable carrier can comprise one or more agents selected from the group consisting of a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, and the like. The selection and quantity of these reagents falls within the professional literacy and routine skills of those having ordinary skill in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, the pharmaceutical composition can be administered by a parenteral route selected from the group consisting of the intraperitoneal injection, the subcutaneous injection, the intramuscular injection, and the intravenous injection.

Definition

The "effective amount" describes herein is the amount of the lipopolysaccharide of the *Parabacteroides goldsteinii* requires for inhibiting the immune response and/or inflammatory response induced by pathogenic lipopolysaccharides in mammalian or human peripheral blood mononuclear cells, macrophages, or B cells, in particular, the immune response and/or inflammatory response induced by lipopolysaccharides of *E. coli* to inhibit inflammatory responses in mammals or humans. The effective amount varies depending on the species or individual being treated, but the effective amount can be determined experimentally by, for example, a dose escalation test.

According to the present invention, the operating procedures and parameter conditions for bacterial culture are within the professional literacy and routine techniques of those having ordinary skill in the art.

According to the present invention, the operating procedures and parameter conditions for culture of peripheral blood mononuclear cells, macrophages, and B cells are within the professional literacy and routine techniques of those having ordinary skill in the art.

According to the present invention, the operating procedures and parameter conditions for isolation and purification of human peripheral blood mononuclear cells are within the professional literacy and routine techniques of those having ordinary skill in the art.

According to the present invention, the operating procedures and parameter conditions for isolation and purification of B cells and induction of differentiation of B cell are within the professional literacy and routine techniques of those having ordinary skill in the art.

According to the present invention, the operating procedures and parameter conditions for purification of lipopolysaccharide are within the professional literacy and routine techniques of those having ordinary skill in the art.

According to the present invention, the operating procedures and parameter conditions for flow cytometer are within the professional literacy and routine techniques of those having ordinary skill in the art.

The "the bacterial component thereof" describes herein is a derivative substance directly or indirectly related to the bacterium when it is cultured, including but not limited to the metabolic product of the bacterium, the structure of the bacterium, the bacteria-related activity and the inactive ingredient, etc.

The Strain of the *Parabacteroides goldsteinii* of the Present Invention

The *Parabacteroides goldsteinii* (*P. goldsteinii*) strain MTS01 used in the examples of the present invention is a probiotic strain, in particular, the lipopolysaccharides (LPS) of the *Parabacteroides goldsteinii* can inhibit the inflammatory responses of an individual induced by lipopolysaccharides of *Escherichia coli* (*E. coli*). The *Parabacteroides goldsteinii* is deposited in Deutsche Sammlung von Mikroorganismen and Zellkulturen (DSMZ; Inhoffenstr. 7B, D-38124 Braunschweig, Germany) on Oct. 29, 2018, and the number is DSM 32939; the *Parabacteroides goldsteinii* is also deposited in the Food Industry Research and Development Institute (Taiwan) on Feb. 15, 2019, and the number is BCRC910869. The *Parabacteroides goldsteinii* is an obligate anaerobe that needs to be cultured in an anaerobic incubator at 37° C. for about 48 hours, wherein the culturing system contains 10% $CO_2$, 10% $H_2$, and 80% $N_2$. The liquid culture medium of the *Parabacteroides goldsteinii* is NIH thioglycollate broth (TGC II) (purchased from BD, USA, No. 225710), and the solid culture medium is Anaerobic blood agar plate (Ana. BAP) (purchased from CREATIVE LIFESCIENCES, Taiwan). The *Parabacteroides goldsteinii* is stored in a −80° C. refrigerator for a long-term preservation, and the protective liquid is 25% glycerin. It does not need special cooling treatment and can be stored by freeze drying to stabilize its activity.

In the examples of the present invention, it was confirmed through cell experiments that the lipopolysaccharide of *Parabacteroides goldsteinii* of the present invention can effectively inhibit the increase in secretion of interleukin-1β in peripheral blood mononuclear cells, the increase in secretion of TNF-α in macrophages, and the increase in expression of surface antigen CD86 and cell proliferation in Naïve B cells, indicating that the lipopolysaccharide of *Parabacteroides goldsteinii* of the present invention can inhibit the immune response induced by the lipopolysaccharide of *E. coli* in human peripheral blood mononuclear cells, macrophages, or B cells, and has immunosuppressive ability; therefore, the lipopolysaccharide of *Parabacteroides goldsteinii* of the present invention can be used for inhibiting the inflammatory response and the preparation of the compositions thereof, and in particular, the lipopolysaccharide of *Parabacteroides goldsteinii* of the present invention can inhibit the immune response caused by pathogenic lipopolysaccharide.

According to the present invention, the probiotic or probiotic bacteria is a microorganism, the cells thereof, the mixed strains, the extracts or the metabolites with a positive effect on the host itself, usually derived from the human body and is beneficial to intestinal health. Probiotic or probiotic bacteria can also refer to certain microorganisms that are externally supplemented and are beneficial to the body. Wherein, the metabolite of the probiotic or probiotic bacteria is a substance which is secreted into the bacterial culture solution after being metabolized by the bacteria, comprising the culture medium for culturing the bacteria.

The present invention provides a method of inhibiting an inflammatory response, comprising administering to a subject in need thereof a composition comprising an effective amount of a lipopolysaccharide of a *Parabacteroides goldsteinii*. At the same time, the present invention also provides a composition for inhibiting the inflammatory responses, which comprises the lipopolysaccharide of *Parabacteroides goldsteinii* and a pharmaceutically acceptable carrier, and the composition is a food, a drink, a nutritional supplement, a health care product, or a medicine.

Characteristic analysis and comparison of lipopolysaccharides of *Parabacteroides goldsteinii* of the present invention, methods and steps for isolating and purifying lipopolysaccharides of *Parabacteroides goldsteinii*, anti-inflammatory activity of lipopolysaccharides of *Parabacteroides goldsteinii* in peripheral blood mononuclear cells, anti-inflammatory activity of lipopolysaccharides of *Parabacteroides goldsteinii* in macrophages, and anti-inflammatory activity of lipopolysaccharides of *Parabacteroides goldsteinii* in B cells will all be described in detail below.

Example 1

Characteristic Analysis and Comparison of Lipopolysaccharides of *Parabacteroides goldsteinii*

In one embodiment of the present invention, the characteristics of the lipopolysaccharides of the *Parabacteroides goldsteinii* MTS01 was analyzed and compared. First, perform a BLAST search of the entire genome of the *Parabacteroides goldsteinii* to identify candidate genes responsible for biosynthetic lipid A; wherein, Blast (Basic Local Alignment Search Tool) is an algorithm used to compare the primary structure of biological sequences (such as the amino acid sequences of different proteins or the DNA sequences of different genes). By comparing with information in a database known to contain several sequences, BLAST is a tool used to find existing sequences that are the same or similar to the sequence to be analyzed, in order to predict its efficacy or role. BLAST is based on KEGG and Search in NCBI-NR's data library.

In this embodiment, the BLAST search was based on *E. coli* MG1655 strain (Genome accession number: U00096) and commercial *Bacteroides dorei* (*B. dorei*) DSM17855 strain, and relevant genes responsible for biosynthetic lipid A were used as a reference point for comparison; wherein, FIG. 1 is the biochemical synthesis pathway of $Kdo_2$-lipid A in *E. coli*, namely the Raetz pathway. As shown in FIG. 1A, uridine diphosphate N-acetylglucosamine (UDP-GlcNAc) is as the starting material of the reaction, and a total of seven enzymes LpxA, LpxC, LpxD, LpxH, LpxB, LpxK, and KdtA are used to synthesize the primary product of lipid A of *E. coli*. The fifth and sixth fluorenyl chains are added to the primary product through two enzymes, LpxL and LpxM, respectively, and lipid A of *E. coli* is completed, namely Kdo$_2$-lipid A in FIG. 1A. It is known that lipid A of *E. coli* usually contains six fluorenyl chains. Lipopolysaccharides of bacteria are mainly composed of lipid A, core oligosaccharide, and O poly-saccharide (or O antigen); wherein, lipid A is the main source of toxicity of lipopolysaccharide, and its main function is to assist lipopolysaccharide to fix on the cell membrane of the strain.

Therefore, BLAST analysis was performed on nine genes related to Kdo$_2$-lipid A synthesis, i.e. LpxA, LpxC, LpxD, LpxH, LpxB, LpxK, KdtA, LpxL, and LpxM of *E. coli*. *Bacteroides dorei* DSM17855 strain belonging to the same genus of *Bacteroides* related to Kdo2-lipid A synthesis were also subjected to BLAST analysis as the comparison group.

The comparison results of BLAST analysis were shown in FIG. 1B; wherein, the leftmost column was the putative genes that may be related to the lipid A synthesis in the *Parabacteroides goldsteinii* MTS01 of the present invention, the middle column was the identity and E value of the putative genes in *E. coli* MG1655 strain; the rightmost column was the identity and E value of the putative genes in *Bacteroides dorei* DSM17855 strain. As shown in FIG. 1B, the results of the analysis and comparison indicate that in the *Parabacteroides goldsteinii* MTS01 of the present invention, the sequence position of the ortholog genes corresponding to LpxA, LpxC, LpxD, LpxH, LpxB, LpxK, KdtA, and LpxL could be found in the *Parabacteroides goldsteinii* MTS01, but the ortholog gene corresponding to LpxM could not be found, and *Bacteroides dorei* DSM17855 strains had the same analysis results. According to previous research, the lipid A of *Parabacteroides goldsteinii* and bacteria of the same genus, such as *Bacteroides thetaiotaomicron*, *Bacteroides dorei*, or *Bacteroides fragilis*, is all penta-acylated instead of hexa-acylated, as mentioned above, LpxM is an enzyme that adds a sixth fluorenyl chain to lipid A, so the BLAST analysis results was in line with the previous research.

It can also be known from the previous research that there is heterogeneity between the lipopolysaccharides of different genus form *Bacteroides*, and as shown in FIG. 1B, the identity of the eight corresponding orthologous genes in the *Parabacteroides goldsteinii* MTS01 of the present invention and the *Bacteroides dorei* DSM17855 strain of the same genus was not high, therefore the results of the BLAST analysis are also consistent with the previous study.

Example 2

Effect of *Parabacteroides goldsteinii* on Inhibiting Inflammatory Response of Peripheral Blood Mononuclear Cell In one embodiment of the present invention, the activity test of lipopolysaccharide of *Parabacteroides goldsteinii* MTS01 to inhibit the inflammatory response of peripheral blood mononuclear cells, PBMC, was performed. However, lipopolysaccharide is located on the cell membrane of bacteria, so the lipopolysaccharide is must first isolated and purified from *Parabacteroides goldsteinii* MTS01 cells to test the direct effect of lipopolysaccharide on anti-inflammatory response.

In the embodiment of the present invention, an RNA isolation reagent (i.e. Tri-Reagent) purification method was used to separate lipopolysaccharide from the entire *Parabacteroides goldsteinii* MTS01 cell. First, *Parabacteroides goldsteinii* MTS01 cells were suspended in a sufficient amount of Tri-Reagent, and then the suspension was subjected under room temperature for fifteen minutes to completely homogenize the cells. Next, $\frac{1}{10}$ volume of chloroform was added to the reaction solution to generate a separated phase, and the mixture was vigorously shaken and mixed, and then reacted at room temperature for another ten minutes. The obtained mixture was centrifuged at 12000 g for 10 minutes to separate the aqueous phase and the organic phase. The aqueous phase solution was transferred to a new 1.5 mL centrifuge tube, and distilled water was added to the organic phase. The steps of mixing, shaking for ten minutes, centrifuging, and collecting the aqueous solution were performed twice to ensure that the lipopolysaccharide in the mixture was completely collected. The aqueous phase solutions were combined and vacuum-dried to obtain the crude lipopolysaccharide purified by Tri-Reagent and the crude lipopolysaccharide was dissolved in 0.375 M magnesium chloride (dissolved in 95% ethanol and stored at −20° C.). Then, after centrifugation at 12000 g for 15 minutes, the supernatant was removed, and the pellet was re-suspended in distilled water and freeze-dried to obtain a fluffy white solid, which is the lipopolysaccharide of *Parabacteroides goldsteinii* MTS01 of the present invention.

The commercial RNA isolation reagents is possible to quickly and easily separate and purify lipopolysaccharide or Lipid A from a small number of bacterial cells. Moreover, this separation and purification method does not require a dedicated separation and purification equipment, and has been used to process a relatively large number of sample purifications. The main functional ingredient in commercial RNA isolation reagents is Tri-Reagent (i.e., Trizol reagent), which is phenol and guanidinium thiocyanate dissolved in aqueous solution. The bacterial cell membrane can be directly destroyed by guanidine thiocyanate in the Tri-Reagent, so there is no need to physically (such as French press) or heat to break the bacterial cell membrane, and the purity of lipopolysaccharide or lipid A purified and isolated by Tri-Reagent is higher than that of conventional means, and the free phosphate pollution in the produced lipopolysaccharide or lipid A product is also lower than that of conventional means.

The peripheral blood mononuclear cells used in one embodiment of the present invention were human peripheral blood mononuclear cells (PBMC) isolated from human blood; wherein, the human peripheral blood mononuclear cell line was isolated through a SepMate™ human peripheral blood mononuclear cell isolation tube (purchased from STEMCELL Technologies Inc., Canada), and cultured with 2×10$^6$ cells per well in a 24-well cultural plate. Human peripheral blood mononuclear cells are composed of lymphocytes, monocytes, and granulocytes.

In order to preliminary understand the immunoregulatory properties of lipopolysaccharide of *Parabacteroides goldsteinii* MTS01 of the present invention on peripheral blood mononuclear cells, the test was first performed to stimulate peripheral blood mononuclear cells with lipopolysaccharide of *Parabacteroides goldsteinii* MTS01 alone. Human peripheral blood mononuclear cells were cultured by the above method, and then 0.01 ng/mL, 0.1 ng/mL, 1 ng/mL, 10 ng/mL, 100 ng/mL, 1000 ng/mL, 10000 ng/mL, or 100,000 ng/mL of the aforementioned lipopolysaccharide of *Parabacteroides goldsteinii* MTS01 of the present invention was respectively added into different wells, and the same concentrations of lipopolysaccharide of *E. coli* O111:B4 strain were as the negative control groups. After added with the lipopolysaccharide, the human peripheral blood mononuclear cells were incubated at 37° C. for 24 hours, and then the same volume of cell culture supernatant from each group was taken out to be analyzed the interleukin-1β (IL-1β) by enzyme-linked immunosorbent assay (ELISA). Wherein, the lipopolysaccharide of *E. coli* O111:B4 strain (purchased from Sigma, USA) was isolated and purified by the same method. *E. coli* O111:B4 strain is a pathogenic *E. coli* strain, and its lipopolysaccharide will induce an individual to develop an inflammatory response.

Figure 2A:
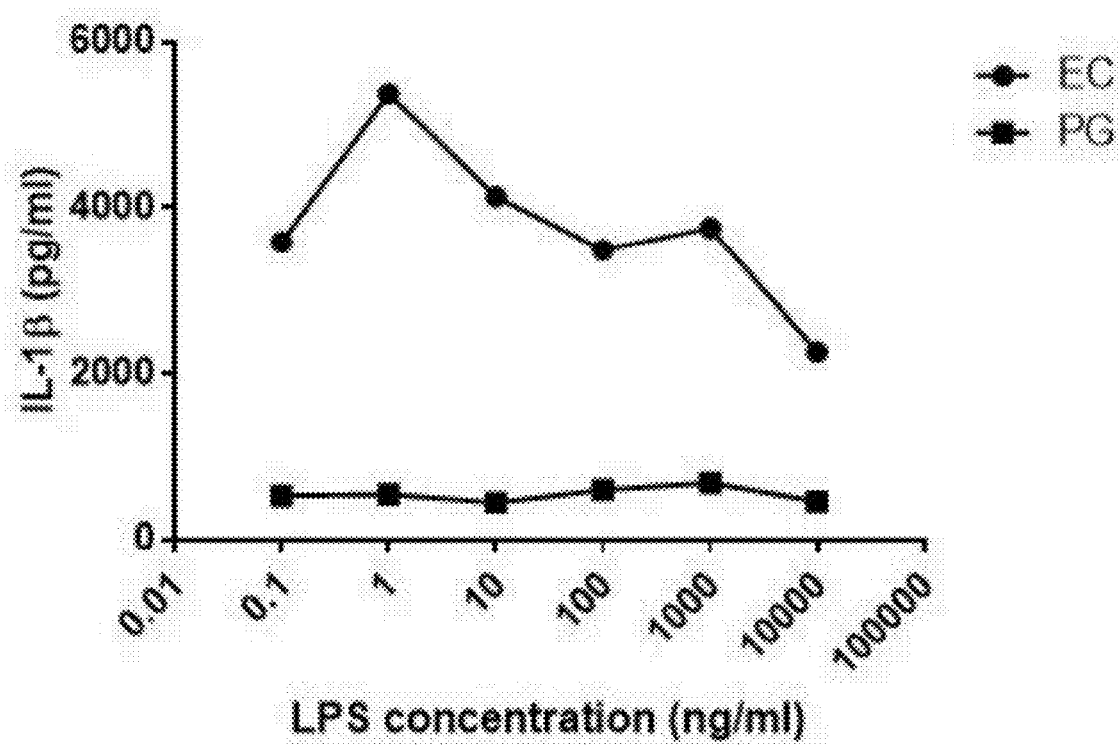
FIG. 2A shows the line graph of the lipopolysaccharide of the *Parabacteroides goldsteinii* of one embodiment of the present invention alone not trigger immune response in peripheral blood mononuclear cells.

The results of the effect of the lipopolysaccharide of *Parabacteroides goldsteinii* MTS01 on peripheral blood mononuclear cells alone were shown in FIG. 2A. As shown in FIG. 2A, after being treated with lipopolysaccharides of *E. coli* O111:B4 strains with different concentrations alone, the amount of interleukin-1β secreted by human peripheral blood mononuclear cells was all above 2000 ng/mL, that is, the lipopolysaccharide of pathogenic *E. coli* could make peripheral blood mononuclear cells secrete cytokines to induce an immune response, indicating that the experimental method could indeed be used to observe the immunomodulatory properties of lipopolysaccharide on peripheral blood mononuclear cells. After being treated with lipopolysaccharides of *Parabacteroides goldsteinii* MTS01 of the present invention with different concentrations alone, the amount of interleukin-1β secreted by human peripheral blood mononuclear cells were significantly lower than those treated with *E. coli* O111:B4 strains at each corresponding concentration. The results indicate that the lipopolysaccharide of *Parabacteroides goldsteinii* MTS01 of the present invention hardly stimulates peripheral blood mononuclear cells to secrete interleukin-1β, that is, it does not induce the peripheral blood mononuclear cells to produce an immune response. Therefore, the lipopolysaccharide of *Parabacteroides goldsteinii* MTS01 of the present invention has low endo-toxicity to individuals.

Next, in order to better understand the immunoregulatory characteristics of lipopolysaccharide of *Parabacteroides goldsteinii* MTS01 of the present invention on peripheral blood mononuclear cells, the test of the anti-inflammatory response effect of lipopolysaccharide of *Parabacteroides goldsteinii* MTS01 of the present invention on peripheral blood mononuclear cells was further performed. First, human peripheral blood mononuclear cells were cultured by the above method, and then lipopolysaccharides of *E. coli* O111:B4 strain and lipopolysaccharides of *Parabacteroides goldsteinii* MTS01 of the present invention were added into different wells respectively with 1:0, 1:1, 1:10, or 1:100 volume ratio (ng/mL) of mixed samples. After added with the lipopolysaccharide, the human peripheral blood mononuclear cells were incubated at 37° C. for 24 hours, and then the same volume of cell culture supernatant from each group was taken out to be analyzed the interleukin-1β (IL-1β) by enzyme-linked immunosorbent assay (ELISA). Wherein, the analysis results of each group were based on the result from 0.1 ng/mL of the lipopolysaccharide of *E. coli* O111:B4 strain.

Figure 2B:
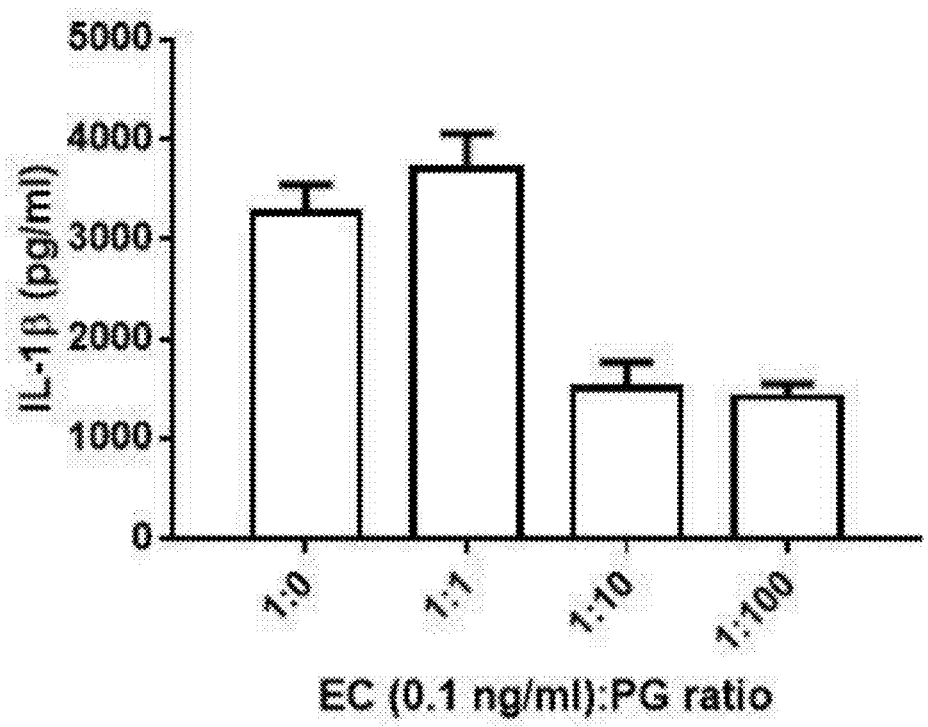
FIG. 2B shows the bar graph of the lipopolysaccharide of the *Parabacteroides goldsteinii* of one embodiment of the present invention inhibiting inflammatory response of peripheral blood mononuclear cells.

The results of the effect of lipopolysaccharides of *Parabacteroides goldsteinii* MTS01 of the present invention on inhibiting the inflammatory response of peripheral blood mononuclear cells were shown in FIG. 2B. As shown in FIG. 2B, after being treated with the mixed samples of 1:10 or 1:100 volume ratios (ng/mL), the amount of interleukin-1β secreted by human peripheral blood mononuclear cells was significantly lower than that treated with the lipopolysaccharide of *E. coli* O111: B4 strain alone or the mixed sample of 1:1 volume ratio (ng/mL). The results indicate that the lipopolysaccharide of *Parabacteroides goldsteinii* MTS01 of the present invention can inhibit the immune response induced by the lipopolysaccharide of *E. coli* in human peripheral blood mononuclear cells, and therefore has the effect of inhibiting the inflammatory response of peripheral blood mononuclear cells.

Example 3

Effect of *Parabacteroides goldsteinii* on Inhibiting Inflammatory Response of Macrophage In the embodiment of the present invention, the activity test of lipopolysaccharide of *Parabacteroides goldsteinii* MTS01 to inhibit the inflammatory response of macrophages was performed. Wherein, the macrophages used in the embodiment of the present invention were murine macrophage RAW264.7 cell line. The murine macrophage cell line was purchased from the American Type Culture Collection (ATCC®) and the number is ATCC® TIB-71™. The macrophages was cultured in DMEM (Dulbecco's Modified Eagle Medium, purchased from Gibco, USA) cell culture medium, containing 10% fetal bovine serum, and 1% antibiotic-antimycotic (purchased from Thermo Fisher Scientific, USA, No. 12100-046), and placed in a 24-well culture plate with $5\times10^5$ cells per well, and cultured in the 37° C. incubator containing 5% carbon dioxide for 24 hours, so that the macrophages could be attached to the bottom of the culture plate.

In order to preliminary understand the immunoregulatory properties of lipopolysaccharide of *Parabacteroides goldsteinii* MTS01 of the present invention on macrophages, the test was first performed to stimulate macrophage with lipopolysaccharide of *Parabacteroides goldsteinii* MTS01 alone. The murine macrophage cells were cultured by the above method, and then 0.01 ng/mL, 0.1 ng/mL, 1 ng/mL, 10 ng/mL, 100 ng/mL, 1000 ng/mL, or 10000 ng/mL of the aforementioned lipopolysaccharide of *Parabacteroides goldsteinii* MTS01 of the present invention was respectively added into different wells, and the same concentrations of lipopolysaccharide of *E. coli* O111:B4 strain were as the negative control groups. After added with the lipopolysaccharide, the murine macrophage cells were incubated at 37° C. for 24 hours, and then the same volume of cell culture supernatant from each group was taken out to be analyzed the tumor necrosis factor-α (TNF-α or TNF-alpha) by ELISA. Wherein, five replicates were performed in each group and statistical analysis was performed by one-wat ANOVA. The values of each group were expressed as ±standard deviation (*$p<0.05$; **$p<0.01$).

Figure 3A:
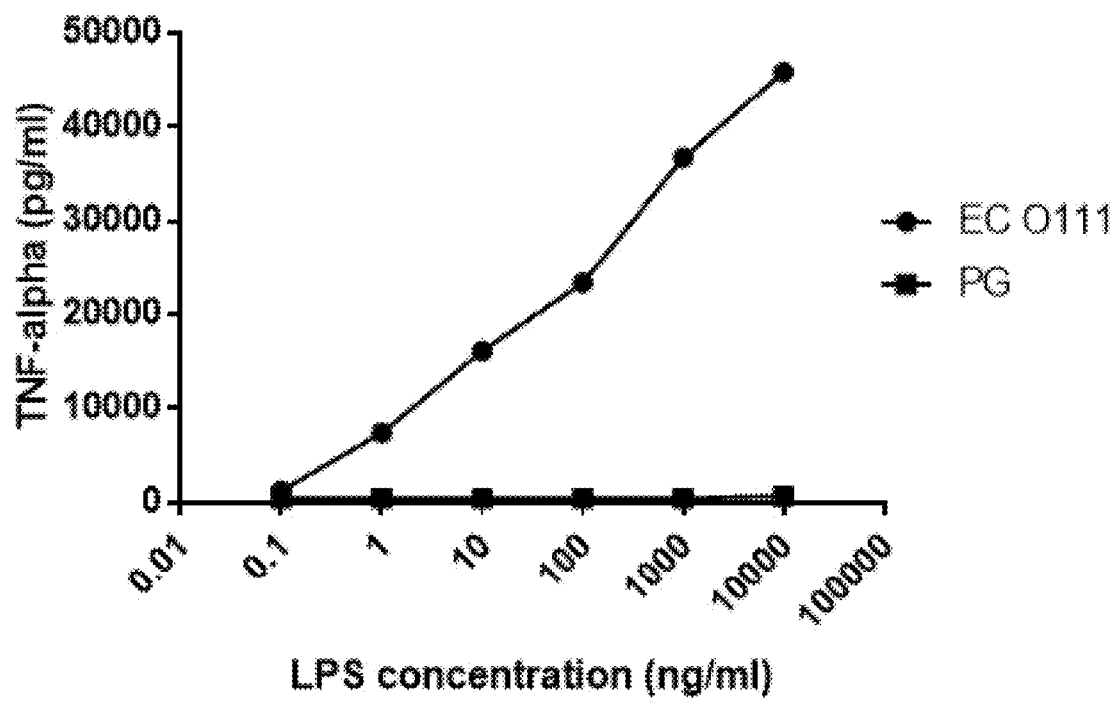
FIG. 3A shows the line graph of the lipopolysaccharide of the *Parabacteroides goldsteinii* of one embodiment of the present invention alone not trigger immune response in macrophages.

The results of the effect of the lipopolysaccharide of *Parabacteroides goldsteinii* MTS01 on macrophages alone were shown in FIG. 3A. As shown in FIG. 3A, after being treated with lipopolysaccharides of *E. coli* O111:B4 strains with different concentrations alone, the amount of TNF-α secreted by murine macrophage cells would increase with increasing concentration, that is, the lipopolysaccharide of pathogenic *E. coli* could make murine macrophage cells secrete cytokines to induce an immune response, indicating that the experimental method could indeed be used to observe the immunomodulatory properties of lipopolysaccharide on macrophages. After being treated with lipopolysaccharides of *Parabacteroides goldsteinii* MTS01 of the present invention with different concentrations alone, the amount of TNF-α secreted by murine macrophage cells were all approached zero and were significantly lower than those treated with *E. coli* O111:B4 strains at each corresponding concentration. The results indicate that the lipopolysaccharide of *Parabacteroides goldsteinii* MTS01 of the present invention would not stimulate macrophages to secrete TNF-α, that is, it does not induce the macrophages to produce an immune response. Therefore, the lipopolysaccharide of *Parabacteroides goldsteinii* MTS01 of the present invention has low endo-toxicity to individuals.

Next, in order to better understand the immunoregulatory characteristics of lipopolysaccharide of *Parabacteroides goldsteinii* MTS01 of the present invention on macrophages, the test of the anti-inflammatory response effect of lipopolysaccharide of *Parabacteroides goldsteinii* MTS01 of the present invention on macrophages was further performed. First, the murine macrophage cells were cultured by the above method, and then lipopolysaccharides of *E. coli* O111:B4 strain and lipopolysaccharides of *Parabacteroides goldsteinii* MTS01 of the present invention were added into different wells respectively with 1:0, 1:1, 1:10, 1:100, 1:1000, or 1:10000 volume ratio (ng/mL) of mixed samples. After added with the lipopolysaccharide, the murine macrophage cells were incubated at 37° C. for 24 hours, and then the same volume of cell culture supernatant from each group was taken out to be analyzed the TNF-α by ELISA. Wherein, the analysis results of each group were based on the result from 1 ng/mL of the lipopolysaccharide of *E. coli* O111: B4 strain. Five replicates were performed in each group and statistical analysis was performed by one-wat ANOVA. The values of each group were expressed as ±standard deviation (*p<0.05; **p<0.01).

Figure 3B:
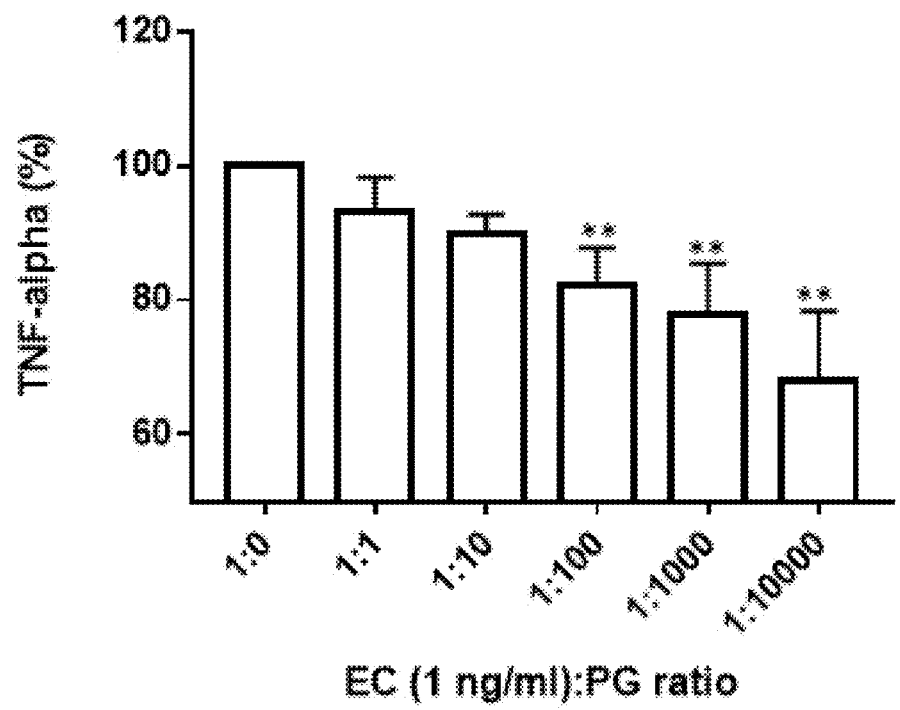
FIG. 3B shows the bar graph of the lipopolysaccharide of the *Parabacteroides goldsteinii* of one embodiment of the present invention inhibiting inflammatory response of macrophages. **$p<0.01$.

The results of the effect of lipopolysaccharides of *Parabacteroides goldsteinii* MTS01 of the present invention on inhibiting the inflammatory response of macrophages were shown in FIG. 3B. As shown in FIG. 3B, after being treated with the mixed samples of 1:1 or 1:10 volume ratios (ng/mL), the amount of TNF-α secreted by murine macrophage cells was lower than that treated with the lipopolysaccharide of *E. coli* O111:B4 strain alone (i.e. 1:0); and after being treated with the mixed samples of 1:100, 1:1000, or 1:10000 volume ratios (ng/mL), the amount of TNF-α secreted by murine macrophage cells was significantly lower than that treated with the lipopolysaccharide of *E. coli* O111:B4 strain alone. The results indicate that the lipopolysaccharide of *Parabacteroides goldsteinii* MTS01 of the present invention can inhibit the immune response induced by the lipopolysaccharide of *E. coli* in macrophages, and therefore has the effect of inhibiting the inflammatory response of peripheral blood monocyte, that is, the lipopolysaccharide of *Parabacteroides goldsteinii* MTS01 of the present invention has the ability of immunoinhibitory, and is a potential factor for inhibiting the inflammatory response induced by *E. coli*.

Example 4

Effect of *Parabacteroides goldsteinii* on Inhibiting Inflammatory Response of B Cell In one embodiment of the present invention, the activity test of lipopolysaccharide of *Parabacteroides goldsteinii* MTS01 to inhibit the inflammatory response of B cells was performed, and the test was performed with Naïve B cells. Wherein, the Naïve B cell was isolated and purified from spleen single cells of non-immune-induced mice by Easy-Sep™ mouse B cell isolation kit (purchased from Stemcell Technologies, UK), and the recovery and purity of the isolated Naïve B cells were analyzed and confirmed by flow cytometry (FACSAria, BD, USA); wherein, the isolated and $4\times10^7$ purified Naïve B cells were re-suspended in flow cytometry staining buffer (phosphate buffered saline buffer, PBS buffer, containing 0.1 fetal bovine serum), and 5-(and-6)-carboxyfluorescein diacetate succinimidyl ester, CFDA-SE (purchased from Molecular Probes, USA) was used for Naïve B cell staining, in which CFDA-SE was added with the final concentration of 5 μM and the Naïve B cells were stained at 37° C. for 10 minutes, and upon diffusion of CFDA-SE into the cells, a highly fluorescent green dye, CFSE, will be generated. After the analysis, the Naïve B cells were immediately washed three times with cold flow cytometry staining buffer, and then the Naïve B cells were re-suspended in the cell culture medium, and were then cultured in a 24-well culture plate at a concentration of $2\times10^6$ cells/mL per well.

CFDA-SE is frequently used in cell proliferation assays, as it is partitioned approximately equally between the progeny so that cell division can be followed as a successive halving of the fluorescence intensity through multiple generational divisions; therefore, the B cell proliferation stimulated with various lipopolysaccharides doses was analyzed by flow cytometry.

According to the previous research, it is known that the Naïve B cells are induced by lipopolysaccharide to induce the Naïve B cells to perform an immune response of antigen presentation. CD86 and CD19 are B-cell-specific antigen-presenting proteins, and CD86 is only expressed after the Naïve B cell differentiation. Therefore, if the Naïve B cell produces an immune response, the expression of the surface antigens of CD86 and the cell proliferation would increase, and it would promote the differentiation of the NaïveB cell into plasma cells, which are the main cells that secrete antibodies and are larger than the Naïve B cells. In addition, if B cells produce an immune response, it would also increase the secretion of TNF-α.

In order to preliminary understand the immunoregulatory properties of lipopolysaccharide of *Parabacteroides goldsteinii* MTS01 of the present invention on B cells, the test was first performed to stimulate B cells with lipopolysaccharide of *Parabacteroides goldsteinii* MTS01 alone. After the Naïve B cells were isolated and purified by the above method, the 100 ng/mL, 1000 ng/mL, or 10000 ng/mL of the aforementioned lipopolysaccharide of *Parabacteroides goldsteinii* MTS01 of the present invention was respectively added into different wells, and the 100 ng/mL, 1000 ng/mL, or 10000 ng/mL of lipopolysaccharide of *E. coli* O111:B4 strain were as the negative control groups. After added with the lipopolysaccharide, the B cells were incubated at 37° C. for 48 hours, flow cytometry was used to analyze the size and the expression of surface antigens of CD86 and proliferation of B cells after immune induction. At the same time, the same volume of cell culture supernatant from each group was taken out to be analyzed the TNF-α secreted from B cells.

Figure 4A:
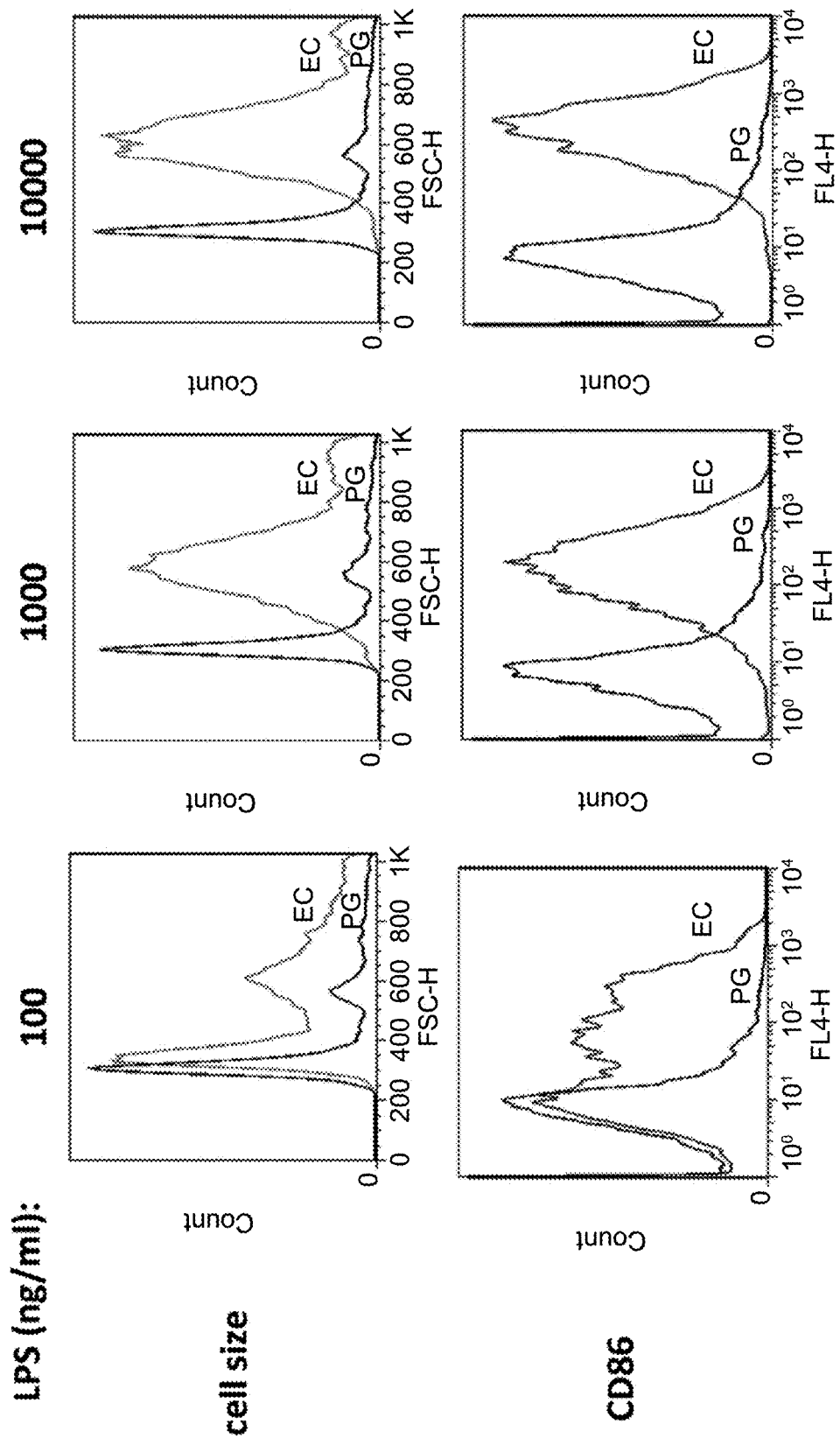
FIG. 4A shows the flow cytometry analysis results of the lipopolysaccharide of the *Parabacteroides goldsteinii* of one embodiment of the present invention not trigger immune response in B cells.
Figure 4B:
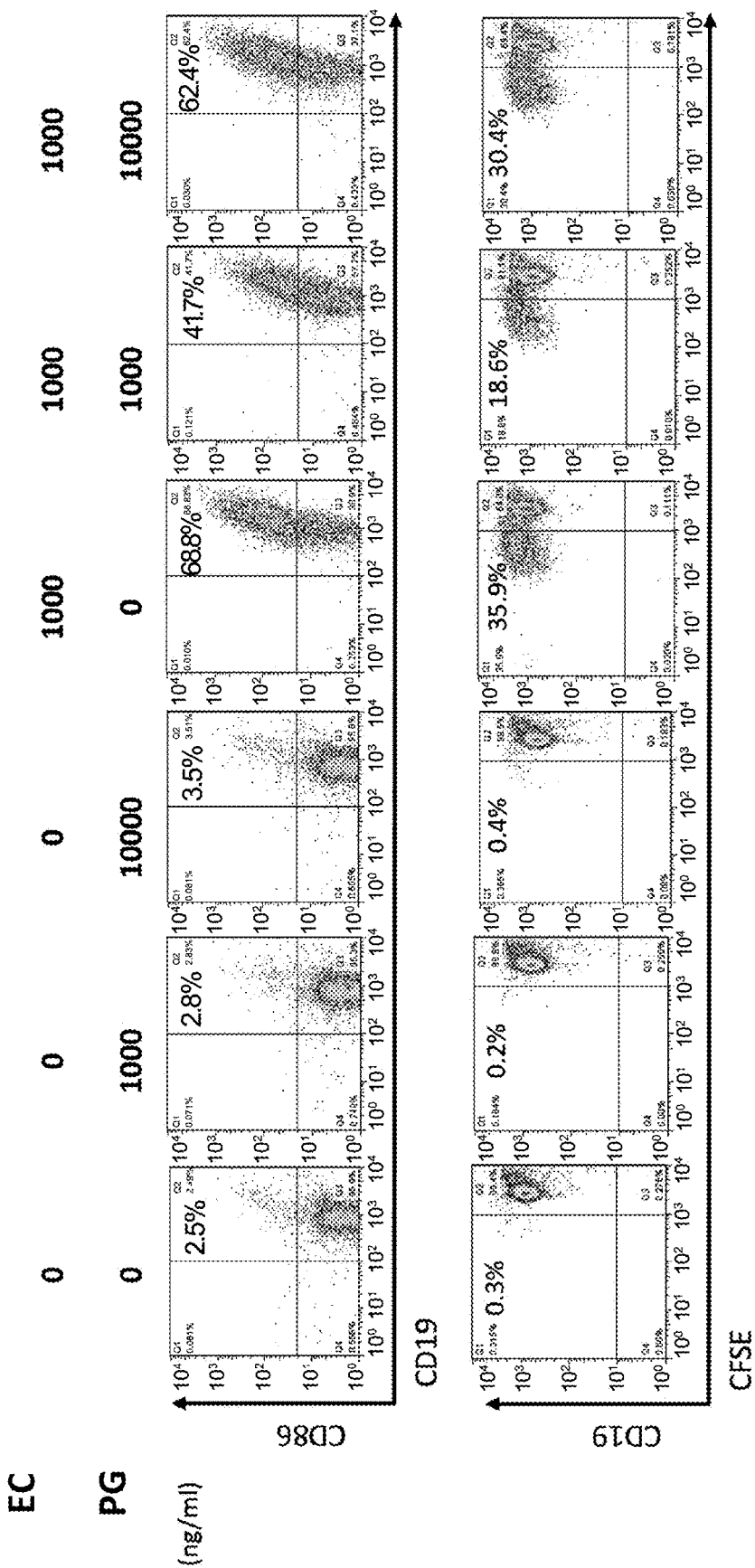
FIG. 4B shows the flow cytometry analysis results of the lipopolysaccharide of the *Parabacteroides goldsteinii* of one embodiment of the present invention inhibiting inflammatory response of B cells.
Figure 4C:
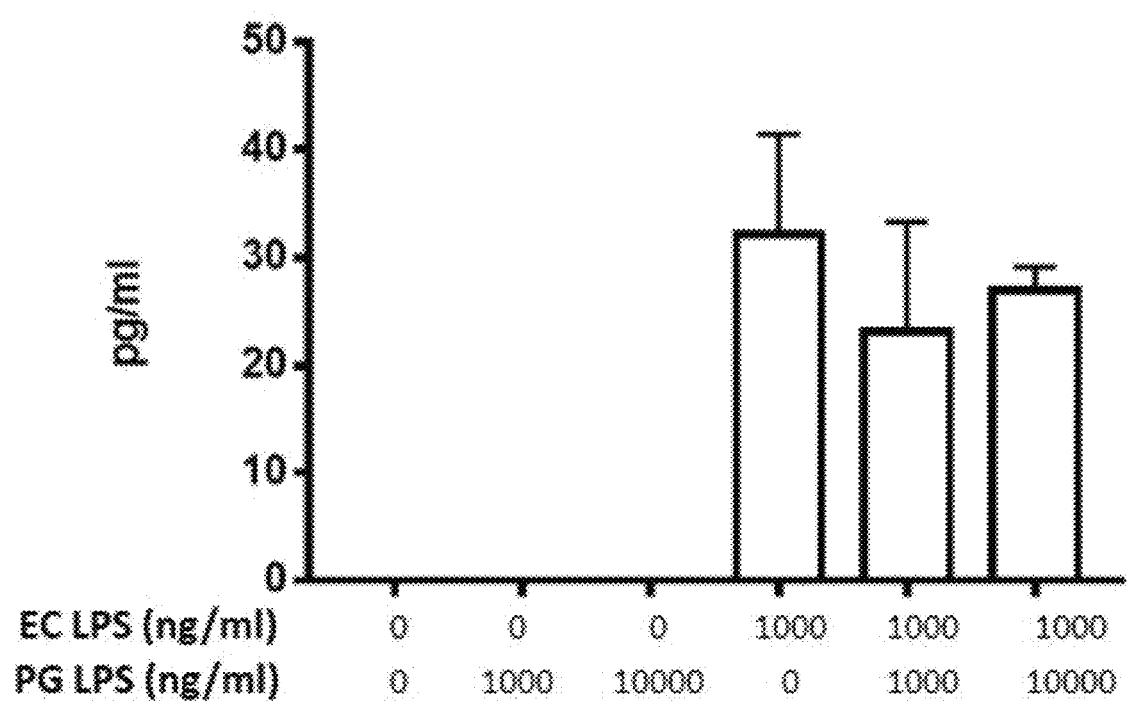
FIG. 4C shows the bar graph of the lipopolysaccharide of the *Parabacteroides goldsteinii* of one embodiment of the present invention inhibiting inflammatory response of B cells.

The results of the effect of the lipopolysaccharide of *Parabacteroides goldsteinii* MTS01 on B cells alone were shown in FIGS. 4A to 4C. As shown in FIG. 4A, after being treated with 100 ng/mL, 1000 ng/mL, and 10000 ng/mL of the lipopolysaccharides of *E. coli* O111:B4 strains alone, the size and the expression of surface antigens of CD86 and proliferation of B cells would increase with increasing concentration. As shown in FIGS. 4B and 4C, after being treated with 1000 ng/mL of the lipopolysaccharides of *E. coli* O111:B4 strains alone, 68.8% of B cells expressed surface antigen of CD86 protein, and 35.9% of B cells were proliferative, and the amount of TNF-α secreted by B cells was about 33 ng/mL. The results indicate that the lipopolysaccharide of pathogenic *E. coli* indeed induces immune response of the Naïve B cells, indicating that the experimental method could indeed be used to observe the immunomodulatory properties of lipopolysaccharide on B cells.

As shown in FIG. 4A, after being treated with 100 ng/mL, 1000 ng/mL, and 10000 ng/mL of the lipopolysaccharides of *Parabacteroides goldsteinii* MTS01 of the present invention, the size and the expression of surface antigens of CD86 of B cells were hardly changed and were significantly smaller and lower than those treated with 100 ng/mL, 1000 ng/mL, and 10000 ng/mL of *E. coli* O111:B4 strains. As shown in FIGS. 4B and 4C, after being treated with 1000 ng/mL or 10000 ng/mL of the lipopolysaccharides of *Parabacteroides goldsteinii* MTS01 of the present invention, respectively, only 2.8% and 3.5% of the B cells expressed surface antigen of CD86 protein, and only 0.2% and 0.4% of the B cells were proliferative, and the amount of TNF-α secreted by B cells approached zero, and these values were all similar to those in B cells which were not treated with any lipopolysaccharide. The results indicate that the lipopolysaccharide of *Parabacteroides goldsteinii* MTS01 of the present invention would not induce the differentiation and secretion of cytokines of the Naïve B cells. Therefore, the lipopolysaccharide of *Parabacteroides goldsteinii* MTS01 of the present invention has low endo-toxicity to individuals and would not induce immune response in Naïve B cells.

Next, in order to better understand the immunoregulatory characteristics of lipopolysaccharide of *Parabacteroides goldsteinii* MTS01 of the present invention on B cells, the test of the anti-inflammatory response effect of lipopolysaccharide of *Parabacteroides goldsteinii* MTS01 of the present invention on B cells was further performed. After the Naïve B cells were isolated and purified by the above method, the lipopolysaccharides of *E. coli* O111:B4 strain and lipopolysaccharides of *Parabacteroides goldsteinii* MTS01 of the present invention were added into different wells respectively with 1000:1000, or 1000:10000 volume ratio (ng/mL) of mixed samples. After added with the lipopolysaccharide, the B cells were incubated at 37° C. for 48 hours, the same volume of cell culture supernatant from each group was taken out to be analyzed the TNF-α secreted from B cells. At the same time, flow cytometry was used to analyze the expression of surface antigen CD86 and cell proliferation of B cells after immune induction.

The results of the effect of lipopolysaccharides of *Parabacteroides goldsteinii* MTS01 of the present invention on inhibiting the inflammatory response of B cells were shown in FIGS. 4B and 4C. As shown in FIGS. 4B and 4C, after being treated with the mixed samples of 1000:1000 or 1000:10000 volume ratios (ng/mL), respectively, 41.7% or 62.4% of B cells expressed surface antigen of CD86 protein, and, respectively, 18.6% or 30.4% of B cells were proliferative, and the amount of TNF-α secreted by B cells was respectively about 20 ng/mL or 36 ng/mL; wherein, the inhibition effect of the mixed samples of 1000:1000 volume ratios (ng/mL) was better than that of the mixed samples of 1000:10000 volume ratios (ng/mL). The results indicate that the lipopolysaccharide of *Parabacteroides goldsteinii* of the present invention can inhibit the immune response of B cells induced by the lipopolysaccharide of *E. coli*, indicating that the lipopolysaccharide of *Parabacteroides goldsteinii* of the present invention has anti-inflammatory activity on B cells.

The use of the lipopolysaccharide of the *Parabacteroides goldsteinii* of the present invention in the inhibition of inflammatory response can be, but is not limited to, oral administration to the subject in need thereof. The composition can be orally administered along with food; therefore, the preparation of the composition comprising the *Parabacteroides goldsteinii* of the present invention can further include a protein, a monosaccharide, a disaccharide, an oligosaccharide, an oligosaccharide, a polysaccharide, a carbohydrate, an amino acid, a lipid, a vitamin, or any combination thereof, and the composition further comprises a pharmaceutically acceptable excipient, carrier, adjuvant, and/or food additive.

Otherwise, the preparation of the composition comprising the lipopolysaccharide of the *Parabacteroides goldsteinii* of the present invention can further comprise a pharmaceutically acceptable carrier or another adjuvant well-known in the art. The composition is in the form of, but is not limited to, a spray gas, a solution, a semi-solid, a solid, a gelatin capsule, a soft capsule, a tablet, an oral strip, a chewing gum, and/or a freeze-dried powder in order to deliver the lipopolysaccharide of the *Parabacteroides goldsteinii* of the present invention to the intestinal tract or to partially or fully colonize to the intestinal tract of subjects. Simultaneously, the lipopolysaccharide of the *Parabacteroides goldsteinii* of the present invention can further use in the preparation of a food, a health food, or a dietary supplement.

In summary, the invention provides a method of inhibiting an inflammatory response, comprising administering to a subject in need thereof a composition comprising an effective amount of a lipopolysaccharide of a *Parabacteroides goldsteinii*. In the *Parabacteroides goldsteinii* of the present invention, the sequence position of orthologous gens corresponding to the gene of LpxA, LpxC, LpxD, LpxH, LpxB, LpxK, KdtA, and LpxL, to the lipid A known in *E. coli* could be found, except LpxM. However, these genes have low identity with *E. coli* MG1655 strain and *Bacteroides dorei* DSM17855 strain. The lipopolysaccharide of *Parabacteroides goldsteinii* of the present invention would not stimulate the secretion of interleukin-1β by peripheral blood mononuclear cells, the secretion of TNF-α by macrophages, and would not induce the Naïve B to express surfaces antigen CD86 and proliferation, which represent the Naïve B cells are induced to differentiate, indicating that the lipopolysaccharide of *Parabacteroides goldsteinii* MTS01 of the present invention would not cause an immune response in peripheral blood mononuclear cells, macrophages, or B cells, that is, it has low endo-toxicity to individuals. Furthermore, the lipopolysaccharide of *Parabacteroides goldsteinii* of the present invention can inhibit the immune response induced by the lipopolysaccharide of *E. coli* in human peripheral blood mononuclear cells, macrophages, or B cells, and has anti-inflammatory activity in peripheral blood mononuclear cells, macrophages, or B cells, and has immunosuppressive ability. Therefore, the lipopolysaccharide of *Parabacteroides goldsteinii* of the present invention can be used for inhibiting the immune response and the preparation of the compositions thereof, and in particular, it can inhibit the inflammatory response caused by pathogenic lipopolysaccharide.

What is claimed is:

1. A method of inhibiting an inflammatory response, comprising:
administering to a subject in need thereof a composition comprising an effective amount of an isolated lipopolysaccharide from a *Parabacteroides goldsteinii*.

2. The method according to claim 1, wherein the isolated lipopolysaccharide inhibits an immune response of a peripheral blood mononuclear cell, a macrophage, or a B cell.

3. The method according to claim 2, wherein the isolated lipopolysaccharide inhibits the peripheral blood mononuclear cell or the macrophage secretes a cytokine.

4. The method according to claim 2, wherein the isolated lipopolysaccharide inhibits differentiation of B cells or secretion of a cytokine.

5. The method according to claim 1, wherein the inflammatory response is induced by a pathogenic lipopolysaccharide.

6. The method according to claim 5, wherein the pathogenic lipopolysaccharide is from an *Escherichia coli*.

7. The method according to claim 1, wherein the *Parabacteroides goldsteinii* is *Parabacteroides goldsteinii* DSM32939.

8. The method according to claim 1, wherein the composition further comprises a pharmaceutically acceptable excipient, carrier, adjuvant, or food additive.

9. The method according to claim 1, wherein the composition is in a form of a spray, a solution, a semi-solid state, a solid state, a gelatin capsule, a soft capsule, a tablet, an oral strip, a chewing gum or a freeze-dried powder.

* * * * *